United States Patent
Kitani et al.

(10) Patent No.: US 8,266,967 B2
(45) Date of Patent: Sep. 18, 2012

(54) STATE DETECTING DEVICE PROVIDED IN A TUBE TO DETECT A STATE OF A LIQUID FLOWING IN THE TUBE

(75) Inventors: Aki Kitani, Hiroshima (JP); Kazuma Sunami, Hiroshima (JP); Shigeharu Yoshimura, Hiroshima (JP); Shogo Kamito, Hiroshima (JP); Junya Fujii, Hiroshima (JP); Mitsuru Kaneko, Hiroshima (JP); Noriaki Nakagawa, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 624 days.

(21) Appl. No.: 12/312,865

(22) PCT Filed: Nov. 21, 2007

(86) PCT No.: PCT/JP2007/072584
§ 371 (c)(1),
(2), (4) Date: Jul. 20, 2009

(87) PCT Pub. No.: WO2008/065950
PCT Pub. Date: Jun. 5, 2008

(65) Prior Publication Data
US 2010/0018317 A1    Jan. 28, 2010

(30) Foreign Application Priority Data

Dec. 1, 2006 (JP) ................................ 2006-326162
Dec. 1, 2006 (JP) ................................ 2006-326220

(51) Int. Cl.
*G01L 7/00* (2006.01)
*G01F 1/00* (2006.01)
(52) U.S. Cl. .......................................... 73/706; 73/861
(58) Field of Classification Search ........................ None
See application file for complete search history.

(56) References Cited

U.S. PATENT DOCUMENTS

| | | | |
|---|---|---|---|
| 4,920,972 A | 5/1990 | Frank et al. | |
| 5,554,113 A | 9/1996 | Novak et al. | |
| 5,614,677 A | 3/1997 | Wamsiedler et al. | |
| 6,880,404 B2 * | 4/2005 | Uberreiter | 73/706 |
| 2004/0050168 A1 | 3/2004 | Uberreiter | |
| 2009/0071258 A1 | 3/2009 | Kouda et al. | |

FOREIGN PATENT DOCUMENTS

| | | |
|---|---|---|
| JP | 2-102638 | 4/1990 |
| JP | 4-502263 | 4/1992 |
| JP | 3526965 | 5/2004 |
| JP | 2007-282996 | 11/2007 |
| WO | 90/06722 | 6/1990 |
| WO | 02/03854 | 1/2002 |
| WO | 2007/123156 | 11/2007 |

OTHER PUBLICATIONS

International Search Report issued Feb. 19, 2008 in the International (PCT) Application of which the present application is the U.S. National Stage.

* cited by examiner

*Primary Examiner* — Lisa Caputo
*Assistant Examiner* — Jermaine Jenkins
(74) *Attorney, Agent, or Firm* — Wenderoth, Lind & Ponack, L.L.P.

(57) ABSTRACT

A state detecting device can efficiently remove air bubbles from a liquid no matter whether the liquid flows forwards or backwards. The state detecting device (1) is provided in a tube to detect a state of a liquid flowing in the tube. The state detecting device (1) includes: a liquid hold part (2) in which the liquid is stored; an inflow part (4) from which the liquid enters the liquid hold part (2); an outflow part (5) from which the liquid exits from the liquid hold part (2); an inlet (8) that is a rear end portion of the inflow part (4); and an outlet (9) that is a front end portion of the outflow part (5). Here, the inlet (8) and the outlet (9) are arranged higher than a center of the liquid hold part (2) in a vertical direction when the state detecting device is provided in the tube.

8 Claims, 6 Drawing Sheets

FIG. 8

| Angle (°) | Displacement | Performance of Air Bubble Removal | Retention |
|---|---|---|---|
| 180 | exist | excellent | little |
| 180 | none | excellent | much |
| 170 | exist | excellent | none |
| 170 | none | excellent | none |
| 150 | exist | excellent | none |
| 150 | none | excellent | none |
| 140 | exist | excellent | none |
| 140 | none | excellent | none |
| 130 | exist | excellent | exist |
| 130 | none | excellent | much |

STATE DETECTING DEVICE PROVIDED IN A TUBE TO DETECT A STATE OF A LIQUID FLOWING IN THE TUBE

TECHNICAL FIELD

The present invention relates to a state detecting device provided in a tube to detect a state of a liquid flowing in the tube.

BACKGROUND ART

Examples of a state detecting device used for monitoring a state of the inside of a circuit in which a liquid flows are: a pressure measuring device detecting a pressure of the liquid flowing in the circuit according to a displacement of a diaphragm provided in a detecting device (see Patent Reference 1); and an optical detecting device detecting a turbidity of the liquid and concentration of specific components in the liquid according to light transmittancy.

When there are air bubbles in these detecting devices, the detecting devices fail to accurately detect the pressure or the light transmittancy. Therefore, it is necessary to remove air bubbles from the detecting devices.

Especially if these detecting devices are arranged in circuits, such as blood circuits, for taking blood from a body to be processed, accurate detection of a pressure or light transmittancy of a liquid flowing in the circuits is desired to provide crucial index for a human life.

The following describes the background art with reference to a blood circuit and a dialysis monitoring device as examples.

Hemodialysis is a treatment for flowing blood taken from a patient through a dialyzer that removes redundant water and waste products from the blood. A fluid channel connected to the patient is called a blood circuit. The blood taken from the patient by a blood pump provided in a dialysis monitoring device flows in the blood circuit, then is purified in the dialyzer connected to the blood circuit, and eventually returns to the body of the patient. A hollow fiber semipermeable membrane is provided in the dialyzer. The hollow fiber semipermeable membrane runs the blood in a hollow fiber and runs dialysate outside the hollow fiber, thereby transferring unnecessary products from the blood to the dialysate in order to remove the unnecessary products from the blood based on a principle of diffusion and filtration via the semipermeable membrane.

In general, the blood and the dialysate move in opposite directions (namely, they are countercurrent flow) so as to improve dialysis efficiency in treatments. Furthermore, the dialysate flows upwards outside the hollow fiber of the dialyzer. Therefore, the blood needs to flow downwards in the dialyzer to be countercurrent flow of the dialysate.

For preparation for the treatment, it is necessary to replace air in the blood circuit and the dialyzer by physiological saline solution or the like before flowing blood in the circuit.

In the preparation, processing of filling physiological saline solution or the like in the circuit using a blood pump of a dialysis monitoring device after setting the circuit in the dialysis monitor device is called "priming". In the priming, a liquid flows downwards in a blood channel in the dialyzer where air is most likely to be left, thereby easily removing air from the circuit. More specifically, a liquid needs to flow downward in treatments and needs to flow upward in the priming. In short, the direction of flowing a liquid is opposite between the treatments and the priming. Therefore, in the priming, the dialyzer is turned over so that an inflow inlet of the dialyzer is positioned low and an outflow outlet of the dialyzer is positioned high, in order to perform preparation such as liquid exchange. In addition, when the priming is switched to the treatments, the dialyzer needs to be re-arranged to a correct direction, which requires considerably complicated processing when a plurality of dialysis patients are to be treated at the same time.

Patent Reference 1: Japanese Patent No. 3526965

DISCLOSURE OF INVENTION

Problems that Invention is to Solve

Therefore, various priming methods have been developed to use the least hands from an initial state where a blood circuit is connected to a dialysis monitoring device to a state of treatment.

One of the priming methods is disclosed to turn a pump in an opposite direction when a blood circuit is provisionally set in a dialysis monitoring device, thereby causing a flow in a direction opposite to a direction of a liquid flowing in treatment. The opposite flow caused by turning the pump in an opposite direction in priming makes it possible to fill a liquid in a dialyzer downwards even if the dialyzer is set in a direction for the treatment.

However, the priming method has a further problem. For example, since the flow direction is opposite between the priming and the treatment, air-air bubble removal is easily performed either in a priming state or in a treatment state (namely, either in priming or in treatment, not both) when a pressure detecting device has a structure as shown in FIG. 1. In more detail, there is a problem that air removal is easy when a liquid flows upwards (namely, forwards) as shown by arrows of FIG. 1 but is difficult when, for example in the priming, the liquid flows in a direction opposite to the arrows. The same problem occurs in an optical detecting device having the similar structure.

The present invention addresses the above problems. It is a first object of the present invention to provide a state detecting device capable of efficiently removing air bubbles from a liquid in the state detecting device both (i) in dialysis processing or the like where the liquid flows in a normal direction and (ii) in priming processing where the liquid flows in a direction opposite to the normal direction.

Furthermore, after conceiving the present invention achieving the first object, a further structure is conceived to improve the effects of the present invention.

More specifically, in the state detecting device having a structure capable of easily removing air bubbles from a liquid flowing no matter whether the liquid flows forwards or backwards, it is observed that the liquid is retained in a liquid hold part depending on a flow velocity or a viscosity of the liquid flowing in a tube.

For example, when the flowing liquid is blood, there is a problem that the retained liquid causes coagulation which prevents accurate pressure detection, for example. In addition, when blood taken from a body is eventually returned to the body in dialysis treatment, the retained liquid cannot be returned to the body and eventually the blood is not completely returned to the body.

The present invention also addresses the above problems. It is a second object of the present invention to provide a state detecting device capable of easily removing air bubbles both from a liquid flowing forwards and from a liquid flowing backwards, and of preventing occurrence of liquid retention as quick as possible.

It should be noted that the above has been described regarding the blood circuits and the dialysis monitoring devices as examples, but the same technologies and problems are found in other devices, blood purification monitoring devices such as blood filter devices, artificial heart-lung devices, and hemoconcentration devices, which take humor from a body and then processes the taken humor.

Means to Solve the Problems

In accordance with an aspect of the present invention for achieving the first object, there is provided a state detecting device provided in a tube to detect a state of a liquid flowing in the tube, the state detecting device including: a liquid hold part in which the liquid is stored; an inflow part from which the liquid enters the liquid hold part; an outflow part from which the liquid exits from the liquid hold part; and an inlet that is a rear end portion of the inflow part; and an outlet that is a front end portion of the outflow part, the inlet and the outlet being positioned higher than a center of the liquid hold part in a vertical direction when the state detecting device is provided in the tube.

With the above structure, the state detecting device can effectively lead air bubbles coming to the surface in the liquid hold part to the outflow part no matter whether the liquid flows forwards or backwards in the tube. As a result, effectiveness of the air bubble removal can be increased. It is preferable that each of the inlet and the outlet is positioned within 10% to 40% of a maximum length of a width direction of the liquid hold part.

It is desirable that the liquid hold part has a top higher than other portions of the liquid hold part, and that the inlet and the outlet are arranged at or close to the top of the liquid hold part.

With the above structure, the state detecting device can further improve the effectiveness of the air bubble removal. In addition, the air bubbles can be removed substantially equally no matter whether the liquid flows forwards or backwards.

It is also desirable that an upper end portion of the inlet, the top of the liquid hold part, and an upper end portion of the outlet are arranged on a substantially same horizontal plane.

With the above structure, the state detecting device can smoothly lead the air bubbles to the outflow part using the liquid no matter whether the liquid flows forwards or backwards. As a result, the air bubbles in the liquid hold part can be much easily removed.

In accordance with another aspect of the present invention for achieving the second object, an angle between an inflow direction axis and an outflow direction axis is less than 180 degrees, the inflow direction axis representing a flowing direction of the liquid entering from the inlet through a center of the inlet, and the outflow direction axis representing a flowing direction of flowing the liquid exiting from the outlet through a center of the outlet.

With the above structure, the state detecting device can stir a liquid that is at least a part of the liquid entering the liquid hold part and that is retained in the liquid hold part. Thereby, it is possible to prevent the liquid from being retained in the liquid hold part.

It is desirable that the angle between the inflow direction axis and the outflow direction axis is in a range from 140 degrees to 170 degrees.

With the above structure, the state detecting device can prevent the liquid from being retained in the liquid hold part and can efficiently discharge air bubbles from the liquid hold part.

It should be noted that the above objects can be achieved also by the flowing state detecting device. The state detecting device in which the inflow part and the outflow part are arranged so that an inflow direction axis and an outflow direction axis do not cross each other, the inflow direction axis representing a flowing direction of the liquid entering from the inlet through a center of the inlet, and the outflow direction axis indicating a flowing direction of the liquid exiting from the outlet through a center of the outlet.

With the above structure, the state detecting device can discharge the liquid, which enters the liquid hold part from the inlet of the inflow part, from the outlet of the outflow by stirring the liquid in the liquid hold part. Thereby, it is possible to prevent the liquid from exiting directly from the outlet before all of liquid which has previously entered has been exited from the liquid hold part. As a result, retention of liquid in the liquid hold part can be prevented.

It is desirable that the liquid hold part has a substantially cylindrical shape, and that the inlet and the outlet are provided on a peripheral wall of the liquid hold part.

With the above structure, the liquid entering the liquid hold part flows circulating along a peripheral wall of the liquid hold part. Thereby, it is possible to easily stir the whole liquid in the liquid hold part. It is also possible to easily achieve both of the prevention of liquid retention and the air bubble removal at the same time.

The state detecting device can, of course, increase the effect of the prevention of liquid retention, by combining the above-described two aspects of the invention.

Effects of the Invention

The sate detecting device according to the present invention can easily and completely remove air bubbles from a liquid in the sate detecting device no matter whether the liquid flows forwards or backwards. Furthermore, the sate detecting device according to the present invention can prevent the liquid from being retained in a liquid hold part as quick as possible no matter whether the liquid flows forwards or backwards, while efficiently achieving the air bubble removal.

BRIEF DESCRIPTION OF DRAWINGS

FIG. 8 is a table showing results of experiments.

NUMERICAL REFERENCES

Figure 1:
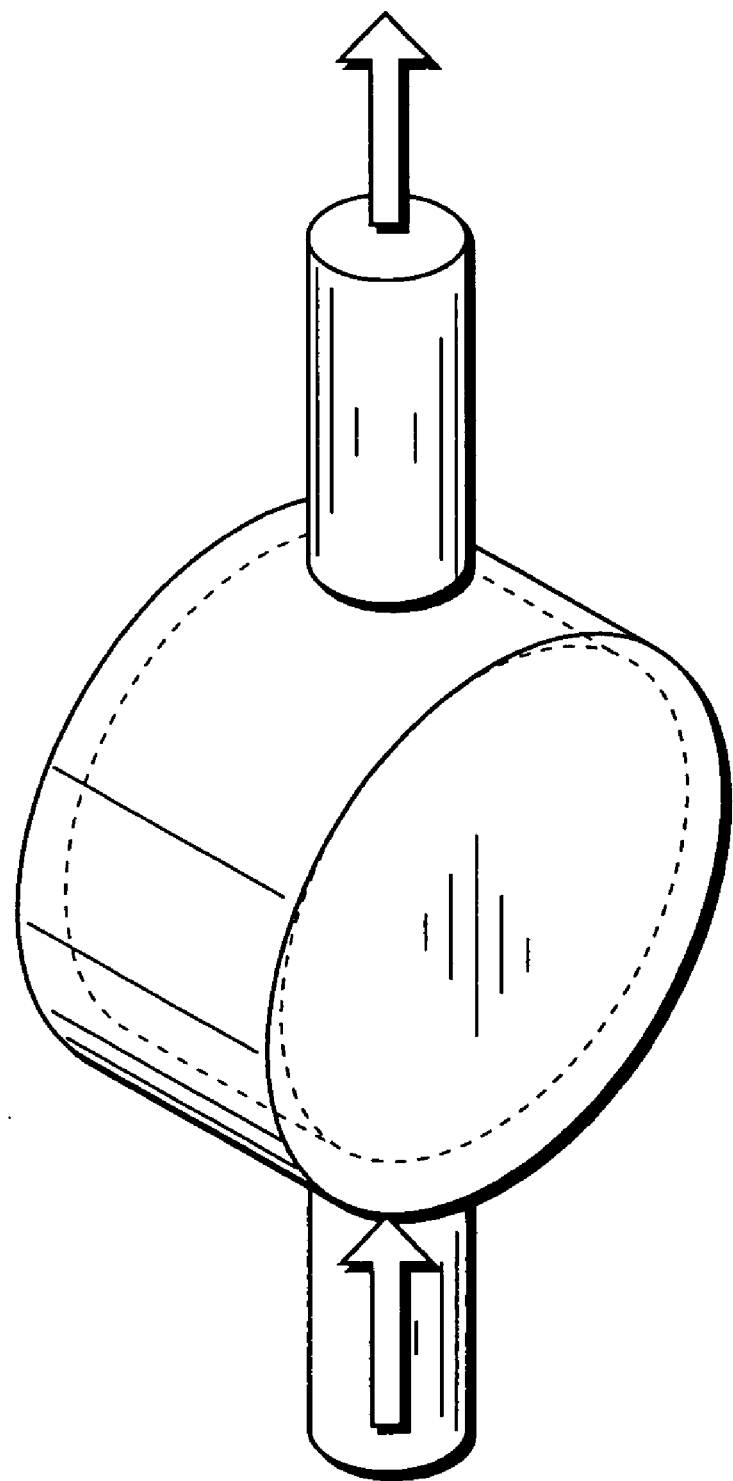
FIG. 1 is a perspective view showing a conventional pressure detecting device.

1 pressure detecting device
2 liquid hold part
3 chassis
4 inflow part
5 outflow part
6 radius extension part
8 inlet
9 outlet 10 vertical axis
11 diaphragm
12 holding ring
13 load cell
14 blood purification monitoring device
17 blood circuit
18 dialysate circuit
19 dialyzer
20 light emitting part
21 light receiving part

BEST MODE FOR CARRYING OUT THE INVENTION

The following describes a pressure detecting device according to an embodiment of the state detecting device of the present invention with reference to the drawings.

Figure 2:
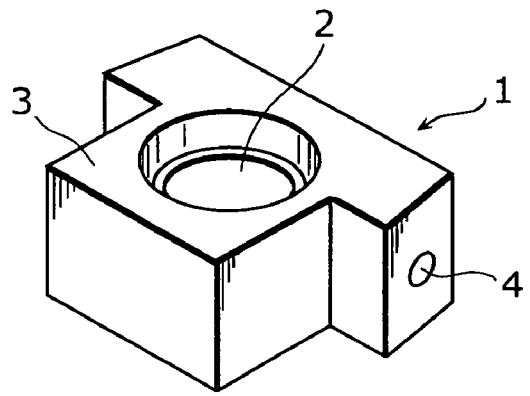
FIG. 2 is a perspective view showing a pressure detecting device from which a diaphragm is removed.

FIG. 2 is a perspective view showing the pressure detecting device having an opening on a surface.

The pressure detecting device 1 of FIG. 2 as the state detecting device is provided in a blood circuit, a dialysate circuit, and the like used in a dialysis monitoring device. The pressure detecting device 1 is a part of a device that detects a pressure of blood or dialysate in such a circuit at real time. The pressure detecting device 1 has a T-shaped chassis 3 that has a cylinder-shaped liquid hold part 2 at the center.

Figure 3:
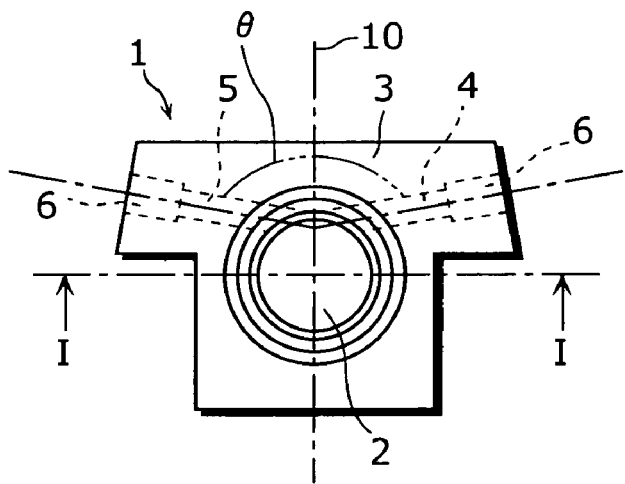
FIG. 3 is a front elevation view of the pressure detecting device.
Figure 4:
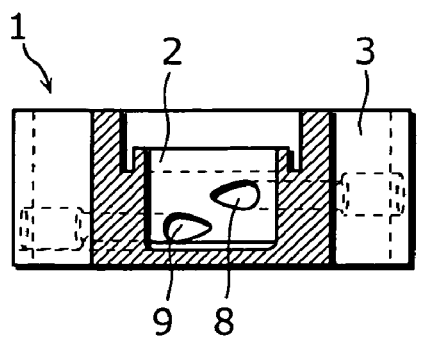
FIG. 4 is a cross-sectional view of the pressure detecting device taken along line I-I of FIG. 3 viewed from a bottom.

FIG. 3 is a front elevation view of the pressure detecting device. In FIG. 3, the pressure detecting device is normally set. FIG. 4 is a cross-sectional view of the pressure detecting device 1 taken along line I-I of FIG. 3 viewed from a bottom.

As shown in FIGS. 3 and 4, the pressure detecting device 1 has an inflow part 4 and an outflow part 5 each of which connects the liquid hold part 2 to the outside of the chassis 3.

Each of the inflow part 4 and the outflow part 5 is a fluid channel directly connected to the liquid hold part 2. In the present embodiment, each of the fluid channels is arranged linearly from the outside of the chassis 3 towards the liquid hold part 2. For the sake of explanation simplicity, it is herein described that the inflow part 4 and the outflow part 5 and later-described inlet 8 and outlet 9 are fixed. However, in priming or the like where a priming liquid flows in circuits and a dialyzer in a direction opposite to a direction of flowing an actually used liquid, the inflow part 4 serves as an outflow part and the inlet 8 serves as an outlet. Likewise, the outflow part 5 serves as an inflow part and the outlet 9 serves as an inlet.

In the present embodiment, an angle θ between the inflow part 4 and the outflow part 5 (since the inflow part 4 and the outflow part 5 are linear, the angle θ is equal to an angle between an inflow direction axis and an outflow direction axis) is set to 160 degrees. When the inflow part 4 and the outflow part 5 are arranged to have the predetermined angle, a part of a liquid entering the liquid hold part 2 reaches a lower portion of the liquid hold part 2, and a liquid existing in the lower portion reaches the outflow part 5. Thereby, the arrangement results in stirring liquid in the liquid hold part 2 to prevent the liquid from being retained in the liquid hold part 2.

It should be noted that the angle θ between the inflow part 4 and the outflow part 5 is not limited to the above. Desirably, the angle is within 170 degrees so that, even if an amount of a liquid entering from the inflow part 4 to the liquid hold par 2 is small, it is possible to prevent the liquid from being retained in the lower portion far from the inlet and the outlet.

It should also be noted that the other end portion (external end portion connected to the outside of the pressure detecting device 1) of each of the inflow part 4 and the outflow part 5 has a radius extension part 6. The radius extension part 6 is a part into which a flexible tube (not shown), which is a fluid channel of a liquid, is inserted forcedly. It is also possible to provide a connector at the external end portion of each of the inflow part 4 and the outflow part 5 so that a tube outside the pressure detecting device 1 can be set in and removed from the connector.

As shown in FIGS. 3 and 4, the liquid hold part 2 has a shape of a cylinder. In order to form the liquid hold part 2, the chassis 3 integrally surrounds a peripheral wall and one end portion of the liquid hold part 2. The other end portion of the liquid hold part 2 is open, not being closed by the chassis 3.

The opened other end portion of the liquid hold part 2 is sealed using a diaphragm that is later described. The liquid hold part 2 is formed by the diaphragm and the chassis 3.

The whole chassis 3 is made of a transparent resin so that a state of a liquid inside the chassis 3 can be seen. Thereby, it is possible to watch a state of blood, a state of dialysate, or a state of flow of a liquid during dialysis.

Furthermore, since the peripheral wall portion of the liquid hold part 2 formed by the chassis 3 is transparent, light can transmits through a liquid stored in the liquid hold part 2. Thereby, for example, a device capable of detecting the transmitted light is provided in the dialysate circuit to detect a change in a light amount of the transmitted light transmitting through the liquid hold part 2. As a result, it is possible to determine a turbidity of the dialysate, namely, whether or not blood is leaked to the dialysate (blood leakage). Moreover, the liquid hold part 2 is a bump-shaped part having a volume greater than that of a tube. Therefore, a distance of transmitting light in a liquid stored in the liquid hold part 2 can be extended. As a result, sensitivity of detecting a turbidity of dialysate or the like can be increased.

The inlet 8 that is an end portion of the inflow part 4 and the outlet 9 that is an end portion of the outflow part 5 are provided on the peripheral wall of the liquid hold part 2. As shown in FIGS. 3 and 4, the inlet 8 and the outlet 9 are positioned higher than the center of a vertical axis 10 that passes through the center of the liquid hold part 2, and also positioned at or close to the top of the liquid hold part 2. Furthermore, the inlet 8 and the outlet 9 are displaced in a thickness direction (a vertical direction in FIG. 4) of the pressure detecting device 1 so that they are symmetric to the vertical axis 10. In other words, the inflow part 4 and the outflow part 5 are arranged so that (i) an inflow direction axis representing a flowing direction of a liquid entering from the inlet 8 through the center of the inlet 8 and (ii) an outflow direction axis representing a flowing direction of a liquid exiting from the outlet 9 through the center of the outlet 9 do not cross each other.

As described above, the inflow part 4 and the outflow part 5 are not arranged on the same plane, which makes it possible to stir a liquid in the liquid hold part 2 in order not to discharge, directly from the outflow part 5, a part of the liquid entering from the inflow part 4. Thereby, it is possible to prevent the liquid from being retained in the liquid hold part 2. In addition, when as described in the present embodiment the inflow part 4 and the outflow part 5 are not arranged on the same plane and the predetermined angle θ (shown in FIG. 3) is set between the inflow part 4 and the outflow part 5, the effect of the prevention of liquid retention in the liquid hold part 2 can be further improved.

Furthermore, as shown in FIG. 3, an upper end portion of the inlet 8 and an upper end portion of the outlet 9 are arranged at the approximately same position in a horizontal direction (a left-right direction in FIG. 3). In addition, a top of the liquid hold part 2 is arranged at the approximately same position as the above position. As described above, when (i) the upper end portions of the inlet 8 and the outlet 9 and (ii) the top of the liquid hold part 2 are arranged on the same plane, air bubbles retained in an upper portion of the liquid hold part 2 are easily transported to the outlet 9 by the liquid entering from the inlet 8. Therefore, it is possible to easily remove air bubbles from the liquid hold part 2 without leaving the air bubbles in the liquid hold part 2. In the present embodiment, since the liquid hold part 2 has a shape of a cylinder, the top is linear.

As described above, by arranging (i) the upper end portions of the inlet 8 and the outlet 9 and (ii) the top of the liquid hold part 2 on the same plane, air bubbles gathering towards the top of the liquid hold part 2 are easily transported to the outlet 9 by the liquid entering from the inlet 8. Therefore, it is possible to easily remove air bubbles without leaving the air bubbles in the liquid hold part 2. In the present embodiment, since the liquid hold part 2 has a shape of a cylinder, the top is linear.

Furthermore, as shown in FIGS. 3 and 4, in the pressure detecting device 1, (i) a shape of the liquid hold part 2, (ii) a position relationship among the liquid hold part 2, the inflow part 4, and the outflow part 5, (iii) tilt of the inflow part 4 and the outflow part 5, (iv) positions of the inlet 8 and the outlet 9, and the like are bilaterally symmetric in FIG. 3, and symmetric to an axis in FIG. 4, so that the state of flowing a liquid is the same even if the inflow part 4 is exchanged by the outflow part 5. Thereby, by arranging a shape and a position relationship of the parts to be symmetric, it is possible to prevent a liquid from being retained in the liquid hold part 2 even if the direction of flowing a liquid is opposite. As a result, air bubbles can be efficiently removed. Therefore, even in priming processing where a liquid flows in an opposite direction, air bubbles can be easily removed from the pressure detecting device.

Figure 5A:
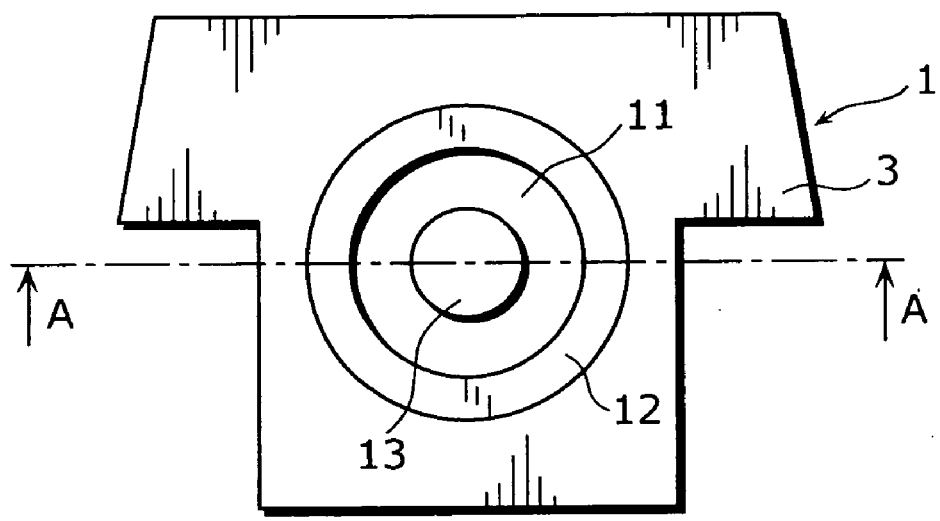
FIG. 5A is a front elevation view showing a state where a diaphragm as a pressure detection part is installed in a chassis.
Figure 5B:
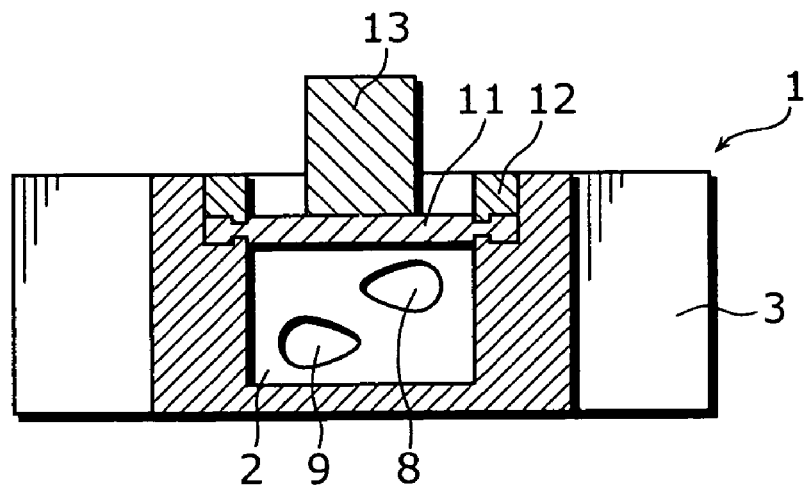
FIG. 5B is a cross-sectional view showing the state where the diaphragm as the pressure detection part is installed in the chassis.

FIG. 5A is a front elevation view showing a state where a diaphragm as a pressure detection part is installed in the chassis. FIG. 5B is a cross-sectional view showing the state taken along line A-A of FIG. 5.

As shown in FIGS. 5A and 5B, one end of the cylinder liquid hold part 2 is sealed by the diaphragm 11 that is transformed by a pressure of a liquid in the liquid hold part 2. This diaphragm 11 is set in the chassis 3 by a holding ring 12 in order not to be removed from the chassis 3.

It should be noted that a load cell 13 connected to the diaphragm 11 is a sensor detecting, as a pressure, a displacement of the center of the diaphragm 11 and its periphery.

Figure 6:
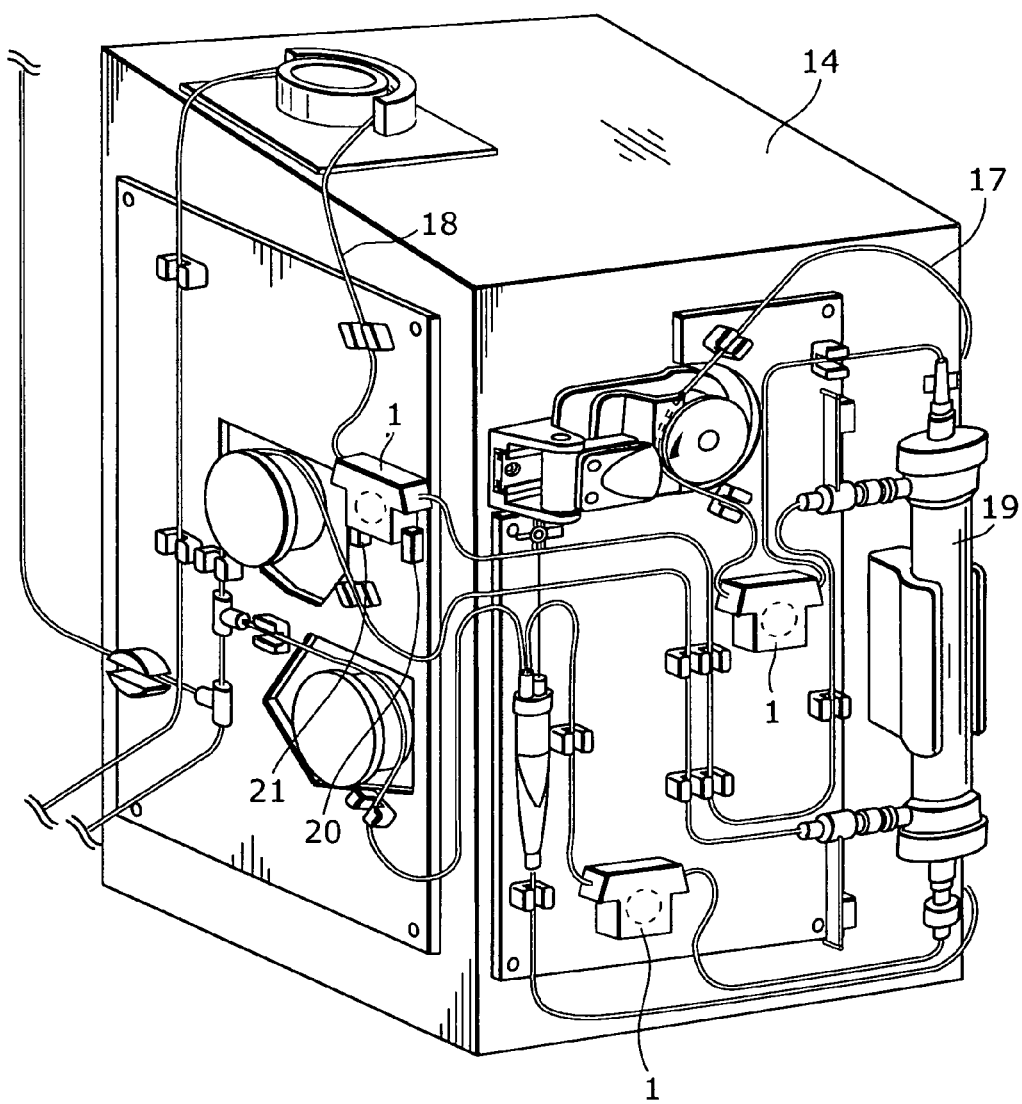
FIG. 6 is a perspective view showing a blood purification monitoring device, and a blood circuit and a dialysate circuit which are set in the blood purification monitoring device.

FIG. 6 is a perspective view showing a blood purification monitoring device 14 suitable for continuous slow treatments, and a blood circuit 17 and a dialysate circuit 18 (replacement fluid circuit or filtrate circuit) which are set in the blood purification monitoring device 14.

As shown in FIG. 6, the pressure detecting devices 1 are provided in the blood circuit 17 before and after the dialyzer 19 used for blood purification. Each of the pressure detecting devices 1 detects a pressure of blood in treatment.

The pressure detecting device 1 is also provided in the dialysate circuit 18 to detect a pressure of dialysate at real time. Furthermore, a light emitting part 20 and a light receiving part 21 are provided at both sides of the pressure detecting device 1 in the dialysate circuit 18. The light receiving part 21 detects a strength of light emitted from the light emitting part 20 to examine whether or not blood leakage occurs in the dialysate. As described above, the pressure detecting device 1 monitors a change in concentration of blood or specific components (change in a received light amount) in the liquid hold part 2, thereby examining a state of the dialysate and a pressure of the dialysate.

EXPERIMENTS

The following describes experiments for examining the effect of the present invention.

The following three experiments have been conducted to examine the effect of the present invention.

(1) A liquid circuit including pressure detecting devices is formed using a predetermined tube. Physiological saline solution is filled in the liquid circuit using a pump. Then, it is visually examined whether or not air bubbles are retained in the pressure detecting devices (checking performance of the air bubble removal).

(2) When the physiological saline solution filled in the liquid circuit is circulated in the liquid circuit using the pump, air bubbles are provided to the liquid circuit using a mixture injection port (not shown). Then, it is visually examined how much the air bubbles are removed from the pressure detecting devices (checking performance of the air bubble removal).

(3) The liquid circuit is filled with cow blood, and then the cow blood is replaced by physiological saline solution. It is visually examined how much the cow blood is retained in the pressure detecting devices after a predetermined time period (checking retention sate).

Figure 7A:
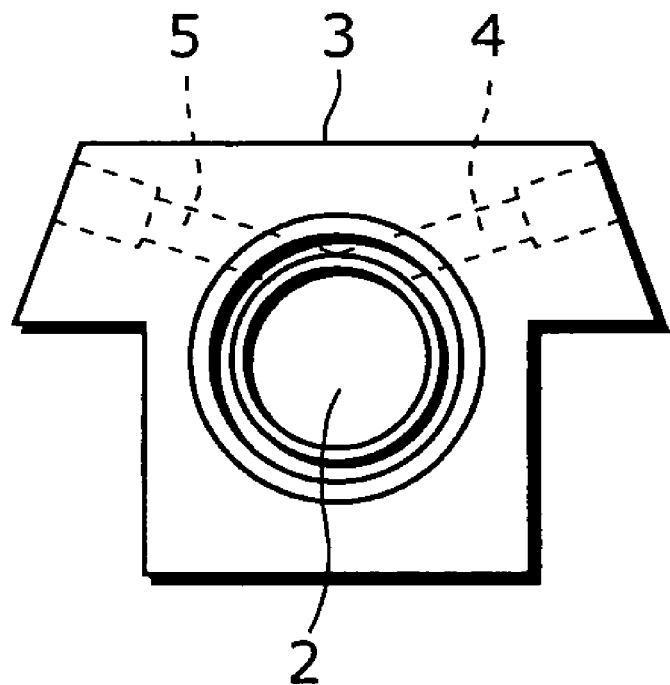
FIG. 7A is a front elevation view showing another structure of the pressure detecting device.
Figure 7B:
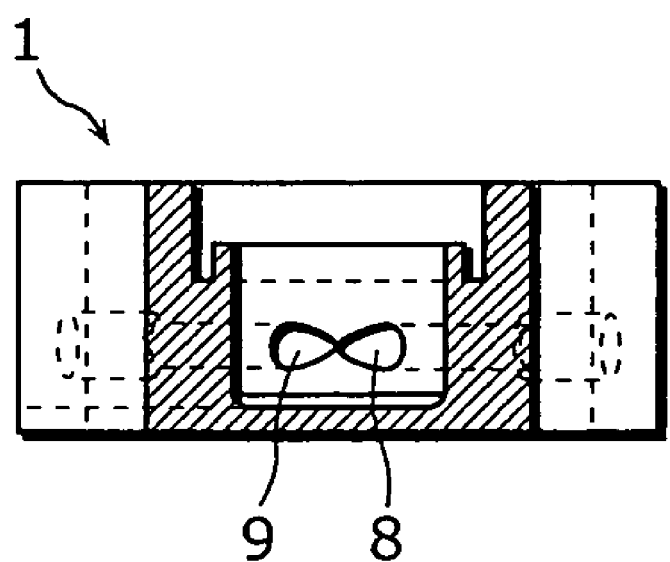
FIG. 7B is a cross-sectional view showing the another structure of the pressure detecting device.

Here, the used pressure detecting devices are: pressure detecting devices in each of which a position relationship between the inlet and the outlet shown in FIG. 4 is displaced in a vertical direction of FIG. 4 (in other words, a displacement exists) and an angle between the inflow part and the outflow part is changed; and pressure detecting devices in each of which a position relationship between the inlet 8 and the outlet 9 is as shown in FIG. 7 (in other words, the inflow direction axis and the outflow direction axis cross each other, or no displacement exists) and an angle between the inflow part 4 and the outflow part 5 is changed.

FIG. 8 is a table showing results of the experiments.

As shown in FIG. 8, regarding the retention state, an amount of the cow blood retained in the pressure detecting device after the predetermined time period tends to be decreased more as the angle θ between the inflow part 4 and the outflow part 5 is decreased. This shows that the effect of the prevention of liquid retention is considerable. However, when the angle θ is greater than 170 degrees, the amount of the retained cow blood is increased and there is also a case where it is almost impossible to replace the cow blood by the physiological saline solution.

Furthermore, it is observed that, even if the angle θ is greater than 170 degrees, when a position relationship between the inlet and the outlet is displaced, the amount of the retained cow blood is decreased more than the situation without displacement, and the displacement of the relationship between the inlet and the outlet tends to improve the retention.

From the above experiments, it is suggested that when the angle θ between the inflow part and the outflow part is set within a range from 140 degrees to 170 degrees, both of (i) the effect of the air bubble removal and (ii) the effect of the retention prevention can be achieved.

It should be noted that the present invention has been described using the embodiment but is not limited to the embodiment.

For example, the state detecting device according to the present invention may not have the pressure detection part (namely, diaphragm). For instance, a state detecting device having a transparent chassis forming a liquid hold part can provide the liquid hold part from which air bubbles can be easily removed regardless of a direction of flowing a liquid. By transmitting light through the liquid hold part, a distance where the liquid intervenes in the light is set longer. Thereby, the state detecting device can detect a turbidity of the liquid with high sensitivity.

Furthermore, the pressure detection is performed not only by measuring a pressure with high accuracy using the diaphragm, but also by roughly detecting plus and minus values of the pressure using a means called pyrrole. The pyrrole is generally used in a blood-purification blood circuit. The pyrrole is a tube having a flexuous radius extension part having a cross section formed/processed to be ellipsoidal in an axis direction of flowing a liquid. The state of a negative pressure in the blood circuit can be examined according to a degree of distortion of the radius extension part.

It should also be noted that a shape of the liquid hold part 2 is not limited to a cylinder but may be a sphere. In the present invention, the liquid hold part 2 may have any desired shape such as a rectangle.

It should also be noted that a shape of the chassis 3 is not limited to the T-character shape, but may be any desired shape. For example, the chassis 3 may be a cylinder corresponding to the shape of the liquid hold part 2.

Industrial Applicability

The present invention can be used as a state detecting device that detects a state of a liquid flowing in a tube. Especially, the state detecting device according to the present invention is preferably used in humor takeout devices each of which takes humor from a body and processes the taken humor.

The invention claimed is:

1. A state detecting device provided in a tube to detect a state of a liquid flowing in the tube, said state detecting device comprising:
   a liquid hold part in which the liquid is stored;
   an inflow part from which the liquid enters said liquid hold part;
   an outflow part from which the liquid exits from said liquid hold part; and
   an inlet that is a rear end portion of said inflow part; and an outlet that is a front end portion of said outflow part, said inlet and said outlet being positioned higher than a center of said liquid hold part in a vertical direction when said state detecting device is provided in the tube,
   wherein said inflow part and said outflow part are arranged so that an inflow direction axis and an outflow direction axis do not cross each other, the inflow direction axis representing a flowing direction of the liquid entering from said inlet through a center of said inlet, and the outflow direction axis representing a flowing direction of the liquid exiting from said outlet through a center of said outlet.

2. The state detecting device according to claim 1, wherein said liquid hold part has a top higher than other portions of said liquid hold part, and said inlet and said outlet are arranged at or close to the top of said liquid hold part.

3. The state detecting device according to claim 1, wherein an upper end portion of said inlet, the top of said liquid hold part, and an upper end portion of said outlet are arranged on a substantially same horizontal plane.

4. The state detecting device according to claim 1, wherein an angle between an inflow direction axis and an outflow direction axis is less than 180 degrees, the inflow direction axis representing a flowing direction of the liquid entering from said inlet through a center of said inlet, and the outflow direction axis representing a flowing direction of flowing the liquid exiting from said outlet through a center of said outlet.

5. The state detecting device according to claim 4, wherein the inflow direction axis and the outflow direction axis are arranged in said liquid hold part in order to prevent the liquid from being retained in a portion farthest from one of said inlet and said outlet in said liquid hold part.

6. The state detecting device according to claim 4, wherein the angle between the inflow direction axis and the outflow direction axis is less than 170 degrees.

7. The state detecting device according to claim 4, wherein the angle between the inflow direction axis and the outflow direction axis is in a range from 140 degrees to 170 degrees.

8. The state detecting device according to claim 1, wherein said liquid hold part has a substantially cylindrical shape, and said inlet and said outlet are provided on a peripheral wall of said liquid hold part.

* * * * *